US009895672B2

(12) United States Patent
Gaserod et al.

(10) Patent No.: US 9,895,672 B2
(45) Date of Patent: Feb. 20, 2018

(54) HIGH STRENGTH SEAMLESS ALGINATE CAPSULES

(75) Inventors: Olav Gaserod, Steinberg (NO); Christian Klein Larsen, Lillestrom (NO); Peder Oscar Andersen, Oslo (NO)

(73) Assignee: DuPont Nutrition USA, Inc., Wilmington, DE (US)

( * ) Notice: Subject to any disclaimer, the term of this patent is extended or adjusted under 35 U.S.C. 154(b) by 624 days.

(21) Appl. No.: 12/874,618

(22) Filed: Sep. 2, 2010

(65) Prior Publication Data
US 2011/0059166 A1 Mar. 10, 2011

Related U.S. Application Data

(60) Provisional application No. 61/241,263, filed on Sep. 10, 2009, provisional application No. 61/241,266, filed on Sep. 10, 2009.

(51) Int. Cl.
| | | |
|---|---|---|
| A61K 9/48 | (2006.01) |
| A23L 1/0532 | (2006.01) |
| A23P 1/04 | (2006.01) |
| B01J 13/04 | (2006.01) |
| A61K 47/02 | (2006.01) |
| A61K 47/36 | (2006.01) |
| B01J 13/20 | (2006.01) |
| A23K 40/30 | (2016.01) |
| A23P 10/30 | (2016.01) |

(52) U.S. Cl.
CPC ............ *B01J 13/046* (2013.01); *A23K 40/30* (2016.05); *A23P 10/30* (2016.08); *A61K 9/4808* (2013.01); *A61K 9/4816* (2013.01); *A61K 9/4833* (2013.01); *A61K 47/02* (2013.01); *A61K 47/36* (2013.01); *B01J 13/20* (2013.01); *B01J 13/206* (2013.01)

(58) Field of Classification Search
CPC ...... A61K 47/02; A61K 47/36; A61K 9/4808; A61K 9/4816; A61K 9/4833
USPC .................................. 424/452; 426/89, 575
See application file for complete search history.

(56) References Cited

U.S. PATENT DOCUMENTS

| | | | |
|---|---|---|---|
| 3,376,199 A | 4/1968 | Coles et al. |
| 4,702,921 A | 10/1987 | Ueda |
| 5,139,783 A * | 8/1992 | Handjani et al. ............. 424/401 |
| 5,385,737 A | 1/1995 | Shigeno et al. |
| 5,502,077 A | 3/1996 | Breivik et al. |
| 5,942,266 A | 8/1999 | Okamura et al. |
| 6,375,981 B1 | 4/2002 | Gilleland et al. |
| 6,458,818 B1 | 10/2002 | Lipari et al. |
| 6,949,256 B2 | 9/2005 | Fonkwe et al. |
| 6,982,095 B2 | 1/2006 | Asada et al. |
| 7,585,538 B2 | 9/2009 | Mangos et al. |
| 7,887,838 B2 | 2/2011 | Archibald et al. |
| 2005/0014852 A1 | 1/2005 | Sewall et al. |
| 2005/0079215 A1 | 4/2005 | Schleifenbaum et al. |
| 2005/0106233 A1* | 5/2005 | Andersen ............. A61K 9/4883 424/451 |
| 2006/0110442 A1* | 5/2006 | Wonschik et al. ............. 424/451 |
| 2006/0233874 A1 | 10/2006 | Suzuki |
| 2009/0208568 A1 | 8/2009 | Hannetel et al. |
| 2009/0208569 A1 | 8/2009 | Modliszewski et al. |
| 2010/0062057 A1* | 3/2010 | Berge et al. ................... 424/455 |
| 2010/0266848 A1 | 10/2010 | Andersen et al. |

FOREIGN PATENT DOCUMENTS

| | | |
|---|---|---|
| EP | 0480729 | 4/1992 |
| EP | 0480729 B1 * | 4/1992 |
| JP | 09-025228 | 1/1997 |
| WO | WO 99/02252 A1 | 1/1999 |
| WO | WO 03/084516 A1 | 10/2003 |

OTHER PUBLICATIONS

Notification of Transmittal of the International Search Report and the Written Opinion of the International Searching Authority, or the Declaration with an International filed of Sep. 2, 2010. dated May 24, 2011.
Database WPI, Week 200476; Thomson Scientific, London, GB; an 2004-775529; XP002741881, & ZA 200 508 253 A (FMC Corp.) Mar. 28, 2007 (Mar. 28, 2007) *Abstract*.
Database WPI, Week 200475; Thomson Scientific, London, GB; an 2004-766698; XP002741882, & CN 1 791 388 A (FMC Corp.) Jun. 21, 2006 (Jun. 21, 2006) *Abstract*.

\* cited by examiner

*Primary Examiner* — Johann R Richter
*Assistant Examiner* — Courtney Brown

(57) ABSTRACT

The invention is directed to a seamless alginate capsule having a film encapsulating a fill material, in which the film comprises alginate, noncrystallizing plasticizer, and glycerol and in which a ratio by weight of noncrystallizing plasticizer to glycerol in the film is between about 1:1 and about 8:1. The invention is also directed to a method of making the seamless alginate capsules and to capsules made by the method. The capsules have excellent breaking strength and are resistant to oxidation of the fill material.

21 Claims, No Drawings

HIGH STRENGTH SEAMLESS ALGINATE CAPSULES

FIELD OF THE INVENTION

The invention is directed to dried seamless capsules comprising an alginate film encapsulating a fill material and methods of manufacture and use thereof.

BACKGROUND

Capsules are widely used in administration of pharmaceuticals and nutritionals to humans and animals. Capsules also have divergent uses, such as serving as reservoirs of plant fertilizer for easy application, of colorants, of food materials or food supplements, and of cosmetic ingredients. Alginate is a convenient material for the film part of the capsule because it can be formed in the process of preparing the capsule.

Seamless alginate capsules having a variety of desirable characteristics are described in WO 03/084516. U.S. Pat. No. 5,385,737 to Shigeno et al. discloses surfactant-containing seamless capsules. U.S. Pat. No. 5,942,266 to Okamura et al. discloses an edible pearly capsule and method for its production. Ueda, in U.S. Pat. No. 4,702,921, discloses a method for preparing fish-egg-like edible products. Gåserød et al. disclose improvements in or relating to capsules in WO 99/02252. Lee et al. disclose microencapsulation for controlled oral drug delivery system in EP 0480729.

Particularly for pharmaceutical and nutraceutical delivery, however, capsules advantageously should be sturdy, dry, stable, resistant to unwanted degradation, able to rapidly release their contents upon suitable delivery, and aesthetically pleasing.

SUMMARY OF THE INVENTION

The invention is generally directed to a seamless alginate capsule comprising a film encapsulating a fill material. The invention is also directed to a method of preparing the capsule.

In one aspect, the seamless alginate capsule comprises a film encapsulating a fill material, wherein the film comprises alginate, glycerol, and a noncrystallizing plasticizer, wherein a weight ratio of the noncrystallizing plasticizer to glycerol is between about 1:1 and about 8:1.

In one aspect, the seamless alginate capsule is resistant to oxidation of an oxidation-sensitive fill material and comprises a film encapsulating the fill material, wherein the film comprises alginate, glycerol, and a noncrystallizing plasticizer.

In another aspect, the seamless alginate capsule comprises a film encapsulating a fill material, wherein the film comprises alginate, glycerol, and noncrystallizing plasticizer and wherein the glycerol comprises between about 6% (wt/wt) and about 22% (wt/wt) of the film and the noncrystallizing plasticizer comprises between about 6% (wt/wt) and about 54% (wt/wt) of the film.

In yet another aspect, the invention comprises a method of making a seamless alginate capsule comprising an alginate film encapsulating a fill material, comprising: a) obtaining or preparing an emulsion comprising oil, water, optionally an emulsifier, and at least one of a water-soluble polyvalent metal salt and an acid, wherein the oil is present in an amount of at least 50% by weight of the emulsion; b) dividing the emulsion into portions; c) adding at least one portion of the emulsion to an aqueous gelling solution comprising alginate to form at least one wet capsule; d) washing the at least one wet capsule with a wash solution to form at least one washed wet capsule; e) contacting the at least one washed wet capsule with a plasticizing solution comprising (i) between about 6% (wt/wt) and about 2% (wt/wt) glycerol and (ii) between about 2% (wt/wt) and about 18% (wt/wt) of a noncrystallizing plasticizer solution, to form at least one plasticized wet capsule; and f) drying the at least one plasticized wet capsule. In this regard, the noncrystallizing plasticizer can be a noncrystallizing sorbitol solution having about 70%-85% solids.

In another aspect, the invention comprises a seamless alginate capsule prepared by the above method.

DETAILED DESCRIPTION OF THE DISCLOSURE

By the term "alginate" is meant a linear unbranched polymer containing (1-4)-linked β-D-mannuronic acid (M) and α-L-guluronic acid (G) residues. Alginates are found in brown seaweeds (class, Phaeophyceae) and other sources. Alginates are not random copolymers, but consist of blocks of similar and alternating residues, for example, MMMM, GGGG, and GMGM, and are generally useful in the form of alginic acid or salts thereof. The alginates from Phaeophyceae seaweeds vary in the proportion of M and include *Lessonia nigrescens* (53-60% M), *Laminaria digitata* (about 59% M), *Macrocystis pyrifera* (about 60% M), *Ecklonia maxima*, and *Laminaria saccharina*.

By the term "capsule" is meant an enclosing structure having a contents (fill material) and surface (film). When substantially dry, the film constrains the fill material. Under some other conditions, the film can permit the fill material to escape. Preferably, the film disintegrates under conditions found in the mammalian small intestine. A finished capsule is substantially dry after exposure to an excess of gas at a relative humidity of 30% or less at room temperature for a day, or the equivalent. Drying means substantially drying. A capsule is "wet" when not substantially dry or when substantially in contact with an aqueous solution.

By the term "noncrystallizing plasticizer" is meant a compound or composition that decreases blooming or recrystallization of the plasticizer substance in or on the capsule film. Glycerol is excluded from the definition of noncrystallizing plasticizer. The noncrystallizing plasticizer can comprise or consist essentially of a mixture of sugar alcohol(s) and dehydro sugar alcohols. In one embodiment the noncrystallizing plasticizer is a mixture of sorbitol and dehydro sugar alcohols.

By the term "noncrystallizing sorbitol" is meant a mixture having sorbitol and anhydrized sorbitol. Anhydrized sorbitol has 1,4-sorbitans and mannitols. POLYSORB® 85/70/00 (Roquette, Lestrem, France) is a suitable noncrystallizing sorbitol. POLYSORB® 85/70/00 is an aqueous solution of 35-45% (wt/wt) sorbitol and 24-28% 1,4-sorbitans (wt/wt) obtained through a partial internal dehydration of sorbitol. POLYSORB® 85/70/00 has about 83% solids content. Sorbitol Special Polyol Solution® (SPI Pharma, Wilmington, Del., USA) is also a suitable noncrystallizing sorbitol. Sorbitol Special Polyol Solution is an aqueous solution of 76% solids including sorbitol, sorbitol anhydrides, and mannitol.

The seamless alginate capsules of the invention have a surprising combination of desirable features, including: a low rate of oxidation of oxidation-sensitive fill material, high break strength of the capsule, high elasticity of the capsule film, and stability of the capsule in moist environments. This combination of features is unexpected because it was not known that changing the capsule composition would improve such disparate other features.

The seamless alginate capsule of the invention can have a ratio of noncrystallizing plasticizer to glycerol (termed the S/G ratio) of between about 1:1 and 8:1 by weight, preferably between about 2:1 and 6:1, and more preferably about 3:1. In one embodiment, the seamless alginate capsules of the invention have a ratio of noncrystallizing sorbitol to glycerol (i.e., the S/G ratio) between about 1:1 and about 8:1. In another embodiment, the S/G ratio is between about 2:1 and about 6:1. In yet another embodiment, the S/G ratio is between about 1:1 and about 4:1. In still another embodiment, the S/G ratio is between about 4:1 and about 9:1. In a preferred embodiment, the S/G ratio is between about 2:1 and 4:1. More specifically, the S/G ratio can be about 1:1, about 2:1, about 3:1, about 4:1, about 5:1, about 6:1, about 7:1, about 8:1, or about 9:1. In one embodiment, the S/G ratio is about 3:1.

The film of the seamless alginate capsule can have up to about 70% by weight total plasticizer. In one embodiment, the total plasticizer is less than 60%, less than 55%, less than 50%, less than 45%, less than 40%, less than 35%, or less than 30% of the film weight. In one embodiment, the total plasticizer is more than about 25%, more than 30%, more than 35%, more than 40%, more than 45%, or more than 50% of the film weight. In one embodiment, the total plasticizer is between about 45% and 55% of the film weight.

The film of the seamless alginate capsules can have between about 6% (wt/wt) glycerol and about 22% (wt/wt) glycerol. In one embodiment, the film of the seamless alginate capsules has between about 10% and 18% glycerol. In one embodiment the film of the seamless alginate capsules has between 12% and 16% glycerol. In another embodiment, the film of the seamless alginate capsules has about 14% glycerol. In one embodiment, the glycerol content of the film does not exceed 17%.

The film of the seamless alginate capsules can have between about 6% (wt/wt) of the noncrystallizing plasticizer and about 54% (wt/wt) of the noncrystallizing plasticizer. In one embodiment, the film of the seamless alginate capsules has between about 6% (wt/wt) noncrystallizing sorbitol and about 54% (wt/wt) noncrystallizing sorbitol. In one embodiment, the film has between about 28% and 46% noncrystallizing sorbitol. In another embodiment, the film has between about 32% and 42% noncrystallizing sorbitol. In another embodiment, the film has between about 34% and 38% noncrystallizing sorbitol. In a preferred embodiment, the film has about 36% noncrystallizing sorbitol.

In one embodiment, the noncrystallizing plasticizer can be maltitol, fructose, propylene glycol or polyoxyethylene glycols, alone or in combination with other plasticizers.

In one embodiment, the dried seamless capsule of the present invention has an alginate shell membrane containing alginate having an average M content of from 50%-62% by weight of the M and G content. More particularly, the average M content of the alginate, by weight of the M and G content, can be 51%, 52%, 53%, 54%, 55%, 56%, 57%, 58%, 59%, 60%, 61% or 62%. The M content may also be in the range of from 53% to 59% by weight of the M and G content.

Alginate having an M content of the present invention is typically obtained from a variety of alginate producing seaweeds. The M content in seaweeds can vary depending on their life cycle at harvest, plant specificity, etc. Seaweeds generally considered to produce alginate having an M content suitable for present invention include *Lessonia nigrescens* (50-62% M), *Laminaria digitata* (about 59% M), *Macrocystis pyrifera* (about 60% M), *Ecklonia maxima* and *Laminaria saccharina*. It is also within the scope of the present invention to use a blend of alginates having various M content provided the M content of all alginates in the blend have an average M content of 53-62% M or an average M content of 50-62% M. The average M content in alginate is typically determined by $^1$H-NMR. The alginate can typically be extracted from the seaweed using, for example, standard commercial extraction processes such as an aqueous process including an acidic pretreatment followed by an alkaline extraction. Such conventional techniques are incorporated herein by reference.

Because the extracted alginates of the present invention having an M content of 50-62% M typically have a high molecular weight and, thus, a high viscosity such as 200-1,000 cps in a 1% solution, the alginate must be degraded to obtain an average viscosity of from 35 to 80 cps when measured in a 3.5% solution at 20° C. using a Brookfield LV viscometer at 60 rpm and spindle #1. The degradation is typically done by conventional heat treatment processes of the alginic acid. These conventional processes are incorporated herein by reference. It is possible to use alginates having varying viscosities outside the scope of 35-80 cps as measured herein provided the average viscosity of all alginates used is within this range. Viscosity measurements on the alginate are performed on a monovalent metal ion salt of the alginate, such as a sodium alginate.

The dried seamless capsules of the present invention desirably have a disintegration time of less than 12 min in an intestinal buffer after pretreatment for 20 minutes in a solution of 0.1 M NaCl and acid (HCl) at pH of 3 at 37° C. and a dry break force strength of at least 10 kg. More particularly, the dried seamless capsule of the present invention has a disintegration time of less than 10 min, less than 8 mins, or less than 6 mins, in an intestinal buffer after pretreatment of 20 mins in aqueous acid at pH of 3. Furthermore, the dried seamless capsule of the present invention has a dry break force strength of at least 12 kg, at least 15 kg, at least 16 kg, at least 17 kg, at least 18, kg, at least 19 kg, at least 20 kg, at least 21 kg, at least 22 kg, at least 23 kg, at least 24 kg, at least 25 kg, at least 26 kg, at least 27 kg, at least 28 kg, or at least 29 kg. The break force strength is measured using a SMS texture analyzer fitted with parallel plates with the capsules lying flat (not on their ends). The intestinal buffer is a simulated intestinal buffer based on USP 28, chapter <2040>, page 2858, except pancreatin is not used. More specifically, the intestinal buffer is made by dissolving 136.0 g $KH_2PO_4$ (Merck, Lot A585477) in 5 L of deionized water, adding 61.6 ml 5N NaOH in 10 L deionized water, adjusting pH to 6.8 and diluting to a final volume of 20 L. The disintegration measurement is as described in USP 28, chapter <2040>, including the chapter about 'Delayed-release (Enteric coated) tablets (incorporated herein by reference).

In one embodiment, the dried seamless capsule comprises an alginate film encapsulating a fill material, wherein: (i) said alginate shell membrane comprises a polyvalent metal ion alginate having: (a) an average M content of from 50%-62% by weight based on the weight of the M and G content, and (b) a viscosity of 35-80 cps when measured as a monovalent metal ion alginate in a 3.5% water solution at 20° C. using a Brookfield LV viscometer at 60 rpm and spindle #1; (ii) said alginate shell membrane encapsulates an oil present in an amount of at least 50% by weight of said fill material; (iii) said dried seamless capsule has a disintegration time of less than 12 minutes in an intestinal buffer (such as described above) after pretreatment for 20 minutes in a solution of 0.1 M NaCl and acid (HCl) at pH of 3 at 37° C.; and (iv) said dried seamless capsule has a dry break force strength of at least 7 kg.

The dried seamless capsules of the present invention encapsulate an oil in an amount of at least 50% by weight of said fill material. The oil itself can be an active ingredient such as a food or a pharmaceutical, nutraceutical, veterinary active ingredient or it can be a carrier for a food or an active ingredient such as a pharmaceutical, nutraceutical or veterinary active agent. The oil may be selected from any oil, or combination of oils, that find utility in an encapsulated form, for example, for use in the pharmaceutical, veterinary, nutraceutical, and food industries. Suitable oils include, without limitation, saturated oils, unsaturated oils including polyunsaturated oils; oils derived from fish, animals, plants, microorganisms, or extracts thereof; oils that are chemical compounds derived by synthetic or other means, or formulations thereof; or oils that are fatty acids, esters, or derivatives thereof. Other oils within the scope of the present invention are those that include naturally occurring emulsifiers. One such oil is soy oil, which contains lecithin. Lecithin is useful in food manufacturing as an emulsifier in products high in fats and oils. Preferred oils within the scope of the present invention are those that are a liquid, or that can be made into a liquid at a temperature in the range of, for example, 20° C. to 95° C.

The oil may be selected from any oil, or combination of oils, that find utility in an encapsulated form, for example, for use in the pharmaceutical, veterinary, nutraceutical, and food industries. Suitable oils include, without limitation, oils derived from marine and non-marine sources including fish, animals, plants, microorganisms, or extracts thereof; oils that are chemical compounds derived by synthetic or other means, or formulations thereof; or oils that are fatty acids, esters, salts or derivatives thereof. Such oils include triglyceride vegetable oils, commonly known as long chain triglycerides such as castor oil, corn oil, cottonseed oil, olive oil, peanut oil, safflower oil, sesame oil, soybean oil, hydrogenated soybean oil and hydrogenated vegetable oils; medium chain triglycerides such as those derived from coconut oil or palm seed oil, monoglycerides, diglycerides and triglycerides. In addition to mixed glycerides there are other oils such as esters of propylene glycol such as mixed diesters of caprylic/capric acids of propylene glycol, esters of saturated coconut and palm kernel oil-derived caprylic, linoleic, succinic or capric fatty acids glycerin or propylene glycol and esters formed between fatty acids and fatty alcohols such as esters formed between capric or caprylic acid and glycerol. Oils that are fatty acids, salts, esters or derivatives thereof are useful in the present invention and are currently the subject of great commercial interest as a result of their beneficial health effects, for example, in reducing risk factors for cardiovascular disease and in the treatment of various metabolic disorders. Oils containing omega-3-fatty acids, salts, esters or derivatives thereof may be used in the present invention. Examples of oils containing such fatty acids, salts, esters, or derivatives thereof include marine oils (e.g., fish oils) that are in the crude or concentrated form and complex oils synthesized by algae. Such marine or algal oils contain important omega-3 polyunsaturated fatty acids such as (all-Z omega-3)-5, 8, 11, 14, 17-eicosapentaenoic acid (EPA) and (all-Z omega-3)-4, 7, 10, 13, 16, 19-docosahexaenoic acid (DHA) that may be contained in varying ratios in the oil of the present invention. One example of such an oil that is useful in the present invention contains at least 80% by weight omega-3-fatty acids (ω-3-fatty acids), salts or derivatives thereof, wherein the EPA and DHA is present in an amount of at least 75% by weight of the total fatty acid content. See, for example, U.S. Pat. No. 5,502,077. Any oil containing DHA and EPA from any source in any DHA/EPA ratio may be used in the present invention.

The oil itself can be an active ingredient such as a food or a pharmaceutical, nutraceutical, veterinary active ingredient or it can be a carrier for a food or an active ingredient such as a pharmaceutical, nutraceutical or veterinary active agent. When the oil is used as a carrier for a food or an active ingredient such as a pharmaceutical, nutraceutical or veterinary active agent, the food or an active ingredient such as a pharmaceutical, nutraceutical or veterinary active agent can be dissolved in the oil or dispersed in the oil.

Examples of pharmaceutical active ingredients that may be dissolved or dispersed in the oil include all active ingredients useful to treat various cardiovascular and metabolic conditions such as statins. Other drugs that can be solubilised in the oil include amprenavir, agenerase, bexarotene, calcitriol, clofazimine, cyclosporine A, digoxin, dronabinol, dutasteride, etoposide, isotretinoin, lopinavir, itraconazole, loratidine, nifedipine, nimodipine, phenobarbital, progesterone, risperidone, ritonavir, saquinavir, sirolimus, tretinoin and valproic acid. Drugs that can be suspended in the oil include those from the classes of gastrointestinal drugs, anti-inflammatory drugs such as non steroidal anti inflammatory drugs, anti microbial drugs, drugs used in the treatment of pain, drugs used to treat metabolic disorders such as obesity, diabetes and rheumatoid arthritis.

The oil is present in the fill material of the capsules in an amount of at least 50% by weight of the fill material, more particularly, at least 60% by weight of the fill material, at least 70% by weight by weight of the fill material, at least 80% by weight fill material, at least 90% by weight of the fill material, or at least 95% by weight of the fill material.

The oil in the fill material can also be in an emulsion such as a water in oil emulsion, oil in water emulsion or water in oil in water emulsion.

The amount of the alginate in the gelling bath was determined to provide a key control of the process viscosities in the preparation of the capsules of the present invention. Applicants determined that in order to make the capsules of the present invention, the amount of the alginate used in the gelling bath is from 3-4% by weight, more particularly, 3.25%-3.75% by weight, of the gelling bath. More particularly, the alginate may be contained in the gelling bath in an amount of 3.5% by weight of the gelling bath. The process viscosities of the gel bath are typically determined by a Brookfield LV viscometer with appropriate spindles and speeds for the target range.

Applicants have determined that the amount and type of the alginate in the gelling bath is a key control of the process viscosity and that process viscosity must be carefully controlled if capsules are to be successfully prepared.

In addition, the agitation of the capsule fragments in the alginate bath and the viscosity of the alginate are connected in making capsules. Alginates having viscosities that require agitation that is too vigorous will deform or destroy the emulsion fragments and the forming capsules, while alginates having viscosities that require very little agitation will result in capsule fragments staying attached to each other either temporarily or permanently. In the first instance, a hole in the shell is formed where the capsule fragments break apart, resulting in leaking capsules. In the second instance, double or twin capsules will be created, containing a double dose and therefore will need to be separated from the batch and discarded. End-to-end twin capsules may survive the gelling step and break apart later in the process, contaminating the other capsules with emulsion. The viscosity of the alginate of the present invention enables appropriate agitations to be employed in the gelling bath that do not cause the problems described hereinabove. The inventors have observed that gelling bath viscosities below 30 cP and above 100 cP undesirably provide more of the problems described above when standard agitation techniques (such as stirring, vibration, or continuous flow over baffles) are employed.

The gelling bath may further contain at least one monovalent salt. The monovalent salt may be at least one of sodium chloride and potassium chloride. Particularly, the monovalent salt may be sodium chloride. The monovalent salt may be present in the gelling bath in an amount of from 0.1-0.5% by weight of the gelling bath, more particularly, in an amount of 0.3% by weight of the gelling bath.

The addition of a monovalent salt in the gelling bath has also been found to provide a preferred means of controlling the level of the monovalent salt in the gelling bath as the calcium reacts with the alginate. This concentration control provides important control of the properties of the resulting capsules.

In the process of the present invention, when a polyvalent salt such as calcium chloride reacts with the sodium alginate in the gelling bath, sodium chloride is generated. Generally, the presence of monovalent salts interferes with the reaction between the gelling polyvalent salt and the alginate and this can have an impact on the resulting gel properties. If the monovalent salt is not added to the alginate solution initially, the concentration of monovalent salts will be essentially zero at the start of capsule formation and will increase significantly during the process, especially if a continuous production mode is chosen. This change will result in variation in capsule quality during the course of the process. The addition of a monovalent salt to the gelling bath provides a stable level of monovalent salts during continuous capsule production, thereby ensuring consistent quality of the capsules both in the wet and dry state.

The gelling bath may also contain additional components to include, without limitation, dyes, colorants, plasticizers; emulsion destabilizers, density adjusters, preservatives, antioxidants, solids, disintegrants, antifoaming agents and other components.

WO 03/084516 discloses typical process conditions and examples of the other components that may be used in the present invention and such disclosure is incorporated herein by reference in its entirety.

Emulsifiers suitable in the context of the present invention are chemical compounds having both a hydrophilic group and lipophilic group wherein the HLB value is in the range of 1 to 19. Examples of such emulsifiers having HLB values in the range of 1 to 19 include, without limitation, glycerin fatty acid esters, lactic acid esters of monoglycerides, lecithins, polyglycerol polyricinoleate, sorbitan esters of fatty acids, succinic acid esters of monoglycerides, calcium stearoyl dilactate, citric acid esters of monoglycerides, diacetyl tartaric acid esters of monoglycerides, polyoxyethylene sorbitan esters of fatty acids, sucrose esters of fatty acids, and other emulsifiers. Emulsifying agents may also include some particulate materials, such as, for example, soot (water-in-oil emulsion stabilizer) or silica powder (oil-in-water emulsion stabilizer) as generally known. Preferred emulsifiers of the present invention are selected from the group of polyoxyethylene(20) sorbitan monopalmitate (Sold under the name TWEEN 40) polyglycerol polyricinoleate (Sold under the name and trademark of PGPR 90, by Danisco, Copenhagen, Denmark), calcium stearoyl-2-lactylate (Sold under the name and trademark of VERV K, by American Ingredients Company, Kansas City, Mo., USA), sorbitan monooleate (Sold under the name and trademark of SPAN 80, by Aldrich Chemical, Milwaukee, Wis., USA), and mixtures thereof. More preferred emulsifiers are polyoxyethylene(20) sorbitan monopalmitate, polyglycerol polyricinoleate, or mixtures thereof.

The emulsions of oil and water of the present invention contain at least one of a water-soluble a polyvalent metal salt or an acid. A water-soluble polyvalent metal salt or acid suitable for use in the present invention includes any inorganic or organic salt or acid that is capable of disassociating into a free ionic state in water, where the ions are capable of forming a gel with the alginate. Suitable salts include, without limitation, the salts of calcium, strontium, barium, aluminum, magnesium, zinc, other salts, and mixtures thereof. A preferred salt is calcium chloride, in either hydrated or anhydrous form. Increasing the salt content in the oil and water emulsion, inter alia, increases the thickness of the polysaccharide gel membrane when the capsules are formed. The salt in the oil and water emulsion is present in at least a gel-forming amount sufficient to adequately form alginate shell membranes surrounding portions of the oil and water emulsion. Preferably, within the scope of the present invention, the salt is present in the oil and water emulsion in an amount of up to 25% by weight of the emulsion, more preferably from 2% by weight to 15% by weight of the emulsion.

In one embodiment of the present invention, the emulsion is an oil-in-water emulsion. The emulsion can be prepared by dissolving a polyvalent metal salt (as discussed above), for example, calcium chloride dihydrate and at least one emulsifier (as discussed above) for example, polyoxyethylene(20) sorbitan monopalmitate, in water. The resultant solution may then be homogenized during which time the oil can be slowly added to form a highly viscous oil-in-water emulsion. The emulsion can have at least 50%, at least 60%, at least 70%, at least 80%, or at least 90%, of oil by weight. A preferable amount of oil present in the oil-in-water emulsion is in an amount of 70% by weight to 98% by weight of the oil, water, emulsifier and water-soluble polyvalent metal salt and acid, more preferably, in an amount of 85% by weight to 95% by weight of the oil, water, emulsifier and water-soluble polyvalent metal salt and acid.

In another embodiment of the present invention, the emulsion is a water-in-oil emulsion. The emulsion can be prepared by adding a water solution of a polyvalent metal salt (as discussed above) and at least one emulsifier (as discussed above), for example, polyglycerol polyricinoleate, to an oil (as discussed above) during which time the mixture can be homogenized to provide the water-in-oil emulsion. A preferable amount of oil present in the water-in-oil emulsion is in an amount of 65% by weight to 85% by weight of the oil, water, emulsifier and water-soluble polyvalent metal salt and acid, more preferably, in an amount of 70% by weight to 80% by weight of the oil, water, emulsifier and water-soluble polyvalent metal salt and acid. As set forth above, soy oil contains the naturally occurring emulsifier lecithin. Water-in-oil emulsions of soy oil may be stable for a period of time long enough so that the emulsion can be encapsulated without inclusion of additional emulsifier.

In yet another embodiment of the present invention, the emulsion is a water-in-oil-in-water emulsion. A water-inoil-in-water emulsion provides a means for encapsulating not only an oil, or an oil-soluble substance, but also, a water-soluble substance, or a water-soluble active ingredient. Accordingly, an inner phase comprised of a solution of a water-soluble substance in water can be added to a middle phase comprised of an oil (as discussed above) and an emulsifier (as discussed above), for example, polyglycerol polyricinoleate, during which time the mixture can be homogenized to form a water-in-oil emulsion. The so-formed water-in-oil emulsion may then be added to an outer phase comprised of a water solution of a monovalent or polyvalent metal salt (as discussed above) and an emulsifier (as discussed above), for example, polyoxyethylene(20) sorbitan monolaurate, during which time the mixture can be homogenized to form a highly viscous water-in-oil-in-water emulsion. A preferable amount of oil present in the water-in-oil-in-water emulsion is in an amount of 60% by weight to 90% by weight of the oil, water, emulsifier and water-soluble polyvalent metal salt and acid, more preferably, in an amount of 70% by weight to 80% by weight of the oil, water, emulsifier and water-soluble polyvalent metal salt and acid.

A preferred emulsion in the context of the present invention is an oil-in-water emulsion as discussed above. A drying process at an elevated temperature and high air flow, for example, at about 30° C. and 0.5-5 m/s, to remove water from the oil-in-water emulsion prior to its encapsulation can eliminate a large portion of water from the encapsulation step, thereby providing a capsule in a relatively dry form, if a capsule in dry form is desired. The length of a separate capsule-drying step can therefore be shortened. Additionally, as an aid to shortening the length of a capsule-drying step if one is desired, some of the water in the emulsion can be replaced with a water-miscible solvent, for example an alcohol of $C_1$-$C_4$ straight or branched carbon length, for example, ethanol.

The seamless capsules of the present invention may also contain encapsulated materials other than the oil. These additional encapsulated materials may be any oil or water soluble pharmaceutical, nutraceutical, or veterinary active ingredients. Thus, such additional encapsulated materials may be dissolved in the oil or dispersed therein.

The capsules of the present invention may take any shape such as spherical, oval, cylindrical or oblong. They may be in dry form may have varying capsule diameters depending on the intended use; e.g., the capsule diameter can be relatively small or somewhat larger, and be in the range of 0.5 millimeter to 35 millimeters, where the alginate film generally has a thickness in the range of 40 µm to 500 µm.

Once dried, the capsules may contain water in the fill material in an amount of less than 5%, less than 3%, or between 0%-0.5%, by weight. Typically, once dried, the emulsion is no longer present in the fill material or it may be found in the form of a dehydrated emulsion maintaining its structure.

The gelled and optionally washed wet capsules are further processed with a plasticizer having a mixture of glycerol and a noncrystallizing plasticizer, such as noncrystallizing sorbitol.

All embodiments of the present invention include those where the fill material in the dried seamless capsule, as well as the emulsion, gelling solution, and plasticizer solution used in the process of making the seamless alginate capsules, do not contain marmelo mucilage.

The present invention is now described in more detail by reference to the following examples, but it should be understood that the invention is not construed as being limited thereto. Unless otherwise indicated herein, all parts, percents, ratios and the like are by weight.

EXAMPLES

Example 1. Plasticizer Bath Formulations

Capsules were prepared using different plasticizer formulations in the plasticizing solution as follows.

An oil-in-water emulsion was prepared according to US 2005/0106233 or as follows. During the entire wet process, solutions were sparged with nitrogen and kept under a nitrogen atmosphere to produce and maintain low oxygen levels. An aqueous phase was prepared by first dissolving EDTA in water (to about 0.1 M) and then adding calcium chloride dehydrate (7 g/10 ml solution). Then Polysorbate 40 (0.8 g) was added and the solution stirred for 20 min. To the aqueous solution, K85EE® (concentrated ω-3 fatty acid ethyl ester from Pronova BioPharma, Lysaker, Norway) was added with slow stirring over the course of about 30 min. to form the emulsion. The emulsion was pumped through an inline mixer at a speed sufficient to yield an emulsion viscosity of about 80000 to 100000 cP. The emulsion was extruded through a nozzle and fragments of about 1.1 g were formed with an 0.1 mm thin wire. The resultant uniform fragments were transferred into an alginate gelling solution bath.

In this example, calcium ions from the calcium chloride salt in the aqueous phase of the emulsion react with the surrounding sodium alginate in the bath solution to form a gel of calcium alginate around the emulsion fragment. This gel, which can be modified, makes up the capsule film, also termed the capsule shell or shell membrane.

The uniform fragments were kept in the gelling bath for approximately 20 minutes at about 20° C. after which the wet capsules were transferred to purified water for approximately 4 hours at about 20° C. The washed capsules were then transferred to an aqueous solution of plasticizer according to Table I for 25-minutes at about 20° C. Capsules were made on laboratory scale and the batch divided into 7 sub batches. Each sub-batch was plasticized in a different plasticizer solution.

TABLE I

Capsule Formulations

| Sample | Plasticizer formulation in plasticizing solution | | |
|---|---|---|---|
| | Glycerol (%) | POLYSORB 85/70/00 (%) | Ratio (S/G) |
| AC 1 | 6 | 2 | 0.33:1 |
| AC 2 | 5 | 7 | 1.4:1 |
| AC 3 | 5 | 10 | 2:1 |
| AC 4 | 4 | 12.5 | 3.1:1 |
| AC 5 | 3 | 15 | 5:1 |
| AC 6 | 2 | 17.5 | 8.8:1 |
| AC 7 | 10 | 0 | 0:1 |

The alginate capsules were dried in a three-step process: a) Initial intensive drying was accomplished using two 3600 m³/hr blowers feeding a drying mesh holding the capsules from beneath; b) When capsule weight fell below 1300 mg, blowers were shut off and overhead fans were turned on; c) After 25 minutes, the fans were shut off and capsules left on the drying mesh for complete drying.

After drying, some capsules were reserved for oxidation measurements. Other capsules were incubated for graduated lengths of time in climate cabinets at 25° C. and 60% RH, in open containers.

After 1, 2, 4, and 8 days, capsules were retrieved from the climate cabinet and analyzed for moisture uptake and break strength or elasticity.

Analysis of the capsule film from capsules plasticized in a 4% glycerol and 12.5% Polysorb® 85/70/00 bath provided a composition of 35% calcium alginate, 14% glycerol, 36% Polysorb solids (that is, sorbitol, sorbitan, and the like), and 15% water, all by weight.

Example 2—Prophetic. Oxidation of Fill Material

Oxidation of fill material can differ with film composition. In general, several of the process steps for preparing capsules need to be operated under an oxygen-free atmosphere in order to achieve low oxygen levels in finished capsules. Control of the drying process is critical to avoid oxidation of the active pharmaceutical ingredient during the drying step.

Glycerol is known as a very good plasticizing agent and gives very pliable capsules in dry conditions. However, alginate capsules with only glycerol as plasticizer can have high oxygen permeability. Noncrystallizing sorbitol is a less effective plasticizing agent such that capsules prepared with high levels of it tend to be brittle in dry conditions.

Capsules are made as in Example 1. After drying the capsules, oxidation is measured by determining anisidine values (AnV) and peroxide values (PV) after 2 weeks storage in open containers at 25° C. and 60% RH. TOTOX is a measure of both primary (peroxide/hydroperoxide) and secondary (anisidine) oxidation, according to the formula: TOTOX=AnV+2PV. The European Pharmacopoeia method for TOTOX measurements is suitable.

The expected oxidation results from two weeks storage in open containers at 25° C. and 60% RH are as follows. Capsules having only glycerol as plasticizer are expected to have an increase in TOTOX values in the middle thirties. Capsules prepared in plasticizing baths having Polysorb/glycerol ratios between 8:1 and 1:1 are expected to have an increase in TOTOX values less than about ten, preferably less than about eight. Capsules prepared using Polysorb/glycerol ratios between about 3:1 and 8:1 are expected to have an increase in TOTOX values less than about 5.

Thus, the plasticizer formulation influences capsule film oxygen permeability. Addition of relatively modest amounts of noncrystallizing sorbitol with glycerol reduces oxidation. Without being limited to a mechanism of action, the oxygen permeability may relate to the water content of the alginate film, as noncrystallizing sorbitol is less hygroscopic than glycerol.

Example 3. Capsule Shell Moisture Uptake

The time course of moisture uptake in the alginate capsule's film was evaluated upon storage in open containers at 25° C. and 60% relative humidity (RH).

An accurate analysis of moisture uptake is measurement of weight increase, which can be measured either on the capsule film and the capsule itself. Moisture level can also be measured by using a moisture analyzer, but some uncertainty results from glycerol (glycerin) evaporation and/or decomposition at elevated temperatures.

The increase in film thickness is another way to follow moisture uptake.

The capsule weight increased after storage in open containers. All the capsules gained weight between zero and one days and were substantially stable after the initial increase. High proportions of noncrystallizing sorbitol as plasticizer generally lead to lower capsule weights. Capsules made with solely glycerol as plasticizer had intermediate weights.

The time course of the absolute weight of the capsule films was measured. The results from the films were similar to the results on the whole capsules but have less variability in the values.

The time course of the normalized gain in capsule film weight was determined. By this measurement, films gained from about 7% for glycerol films to about 20% for 3.1 noncrystallizing sorbitol/glycerol (S/G) films, at one day, and from about 11% for glycerol films to 20% for 3.1 S/G films at eight days.

Due to the high glycerol level, leaking of glycerol upon storage was seen on AC-7 (10% glycerol) capsules. Some of the glycerol on the capsule surface was cleaned off these capsules before measurements. Moreover, some of the capsule material leaked out of the shells. These factors skew the weight analyses and film thickness analyses.

Example 4. Film Thickness and Dry Matter Content

The thickness of the film of the alginate capsules was measured by calibrated optical microscopy. The film thickness development during the stability testing period was determined Film thickness generally increased with increasing sorbitol content. The film thickness increased from day zero to day one for most capsules and was generally stable after day one.

The time course of film dry matter content was measured for capsules stores as in Example 3. The dry matter content decreased for all capsules from day zero to day one and was substantially stable after day one. For example, AC 1 capsules decreased from about 79% dry matter at day zero to about 70% at day one, and AC 6 capsules decreased from about 90% at day zero to about 81% at day one.

Thus, the capsule film picked up moisture quickly at the stability settings tested. Increased plasticizer level gave increased film thickness and film weight. The formulation with highest level of sorbitol had the lowest moisture uptake, by percent. The moisture uptake in AC 5 and AC 6 was low relative to the other capsules. These samples had a film dry matter content above 80% after 8 days storage. AC 4 capsules had a film dry matter content of approximately 80% after 8 days storage. The other four formulations had film dry matter contents of about 75%.

Example 5. Capsule Break Strength and Elasticity

The time course of break strength and elasticity of capsules was evaluated at start up, dry conditions (day zero) and upon storage for graduated periods of time in open containers at 25° C. and 60% relative humidity (RH).

Capsule break strength and elasticity are best measured using an SMS texture analyzer using parallel plates. Capsule break strength was evaluated with capsules lying flat, not standing on end. Capsule brittleness only increased when noncrystallizing sorbitol was used as plasticizer at high levels and capsules were stored under dry conditions.

Capsules were made as in Example 1. The capsules were incubated at 25° C. and 60% RH, on open trays in such a way that the capsule bed layer comprised a either single or double layer of capsules. After 1, 2, 4, and 8 days, capsules were retrieved from the climate cabinet and analyzed for moisture uptake and break strength or elasticity.

The break strength was evaluated over the course of storage for 8 days. Most of the capsule formulations had substantially stable break strengths over time. AC 4, AC 5, and AC 6 had small decreases in strength over the course of day zero to day two and AC 1 and AC 2 increased in break strength slightly over the same time period.

The development of elasticity was measured. Elasticity is the force needed to compress the capsules 0.5 mm (force of deformation). Thus, a higher value indicates a harder, less elastic capsule. All capsule formulations increased in elasticity between day zero and day one, although the glycerol capsules, AC 7, showed the least percentage gain.

Example 6. Brittleness

Brittleness was evaluated by a drop test. Table II shows the drop test results (number of capsules that survived undamaged out of 10 capsules after a 1.5 meter free fall into a steel bucket) at start up conditions, which were approximately 30% RH and 23° C. These conditions are regarded as relatively dry, and represent "dry conditions."

TABLE II

Drop Test Results

| Samples | Passed |
| --- | --- |
| AC 1 | 10 |
| AC 2 | 10 |
| AC 3 | 9 |
| AC 4 | 10 |
| AC 5 | 8 |
| AC 6 | 4 |
| AC 7 | 10 |

The drop test at dry conditions clearly shows differences between the plasticizer bath formulations. Formulations with higher levels of glycerol in the bath survive the drop test, whereas formulations with a very low level of glycerol break more easily. AC 6 has a brittle shell.

Example 7. Core Conversion

In this example Applicants evaluated how the plasticizer formulation affects the conversion of the emulsion into a single oil phase. The emulsion apparently converts from a stable emulsion to a liquid oil phase upon drying. Several parameters affect the conversion process, and the plasticizer formulation is one of these. To evaluate core conversion, capsules were cut open and examined visually.

Capsules were prepared according to Example 1. After 1, 2, 4, and 8 days, capsules were retrieved from the climate cabinet and analyzed for core conversion.

The results are shown in Table III, which shows the percentage of the core that has not converted at the time of measurement.

TABLE III

Degree of Conversion of the Emulsion

| Samples | Glycerol (%) | POLYSORB 85/70/00 (%) | Non-converted emulsion (%) Time (days) | | | | |
| --- | --- | --- | --- | --- | --- | --- | --- |
| | | | 0 | 1 | 2 | 4 | 8 |
| AC 1 | 6 | 2 | 0 | 0 | 0 | 0 | 0 |
| AC 2 | 5 | 7 | 0 | 0 | 0 | 0 | 0-1 |

TABLE III-continued

Degree of Conversion of the Emulsion

| Samples | Glycerol (%) | POLYSORB 85/70/00 (%) | Non-converted emulsion (%) Time (days) | | | | |
| --- | --- | --- | --- | --- | --- | --- | --- |
| | | | 0 | 1 | 2 | 4 | 8 |
| AC 3 | 5 | 10 | 0 | 0 | 1 | 1-2 | 1-2 |
| AC 4 | 4 | 12.5 | 1-2 | 1 | 1-2 | 1-2 | 1-2 |
| AC 5 | 3 | 15 | 5 | 5 | 5-10 | 1-5 | 10-20 |
| AC 6 | 2 | 17.5 | 5-10 | 10 | 10-20 | 10-20 | 10-20 |
| AC 7 | 10 | 0 | 0 | 0 | 0 | 0 | 0 |

Thus, there is a clear dependence between degree of conversion and plasticizer formulation. Increased level of noncrystallizing sorbitol and reduced level of glycerol leads to slower conversion and conversion to a lower extent. Under these conditions, AC 5 and AC 6 have a high likelihood of an unconverted emulsion inside the capsules, both after production and upon storage.

Example 8. Oxidation of Fill Material

Oxidation of fill material can differ with film composition. In general, several of the process steps need to be operated under an oxygen-free atmosphere in order to achieve low oxygen levels in finished capsules. Control of the drying process is critical to avoid oxidation of the active pharmaceutical ingredient during the drying step. Further, it has been shown that the alginate capsule stability in closed containers with glycerol as sole plasticizer is relatively low with respect to oxidation and that use of noncrystallizing sorbitol as the sole plasticizer results in alginate capsules having low elasticity.

Glycerol is known as a very good plasticizing agent and gives very pliable capsules in dry conditions. However, alginate capsules with only glycerol as plasticizer can have high oxygen permeability. Noncrystallizing sorbitol is a less effective plasticizing agent, and ensures lower film oxygen permeability. However, sorbitol capsules tend to be brittle in dry conditions (see drop test section).

Capsules were made as in Example 1. After drying the capsules, oxidation was measured by determining anisidine values (AnV) and peroxide values (PV) after 2 weeks storage in open containers at 25° C. and 60% RH. TOTOX is a measure of both primary (peroxide/hydroperoxide) and secondary (anisidine) measures, according to the formula: TOTOX=AnV+2 PV. TOTOX can be measured according to the method of the European Pharmacopoeia.

The oxidation results are shown in Table IV.

TABLE IV

Oxidation of Capsule Fill Material

| Batch | Increase in TOTOX value |
| --- | --- |
| AC 1 | NA |
| AC 2 | 8 |
| AC 3 | 7 |
| AC 4 | 3 |
| AC 5 | 5 |
| AC 6 | 3 |
| AC 7 | 34 |

Thus, from Table IV, the plasticizer formulation has a strong influence on capsule film oxygen permeability and hence oxidation of the fill material oil. Even relatively modest amounts of noncrystallizing sorbitol with glycerol reduce oxidation. A higher level of glycerol leads higher oxidation levels. Noncrystallizing sorbitol is a good plasticizer with regard to limiting oxidation. All the capsules having sorbitol have much lower oxidation rates than capsules having glycerol without sorbitol. See Table IV. Without being limited to a mechanism of action, the oxygen permeability may relate to the water content of the alginate film, as sorbitol does not pick up as much moisture as glycerol. Of the formulations tested, AC 4, AC 5, and AC 6 have especially acceptable oxygen permeability properties.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. All publications, patents, and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

It is claimed:

1. A seamless alginate capsule comprising a film encapsulating a fill material, wherein the film comprises alginate, glycerol, and a noncrystallizing plasticizer, wherein: (i) a weight ratio of the noncrystallizing plasticizer to glycerol is between about 1:1 and about 8:1; (ii) the total weight of plasticizer in said film is from 35-70% by weight of the film; and (iii) said capsule has a disintegration time of less than 12 minutes in an intestinal buffer after pretreatment for 20 minutes in a solution of 0.1 M NaCl and acid (HCl) at pH of 3 at 37° C.

2. The capsule of claim 1, wherein the ratio is between about 2:1 and about 6:1.

3. The capsule of claim 1, wherein the ratio is about 3:1.

4. The capsule of claim 1, wherein the glycerol comprises between about 6% (wt/wt) and about 22% (wt/wt) of the film or the noncrystallizing plasticizer comprises between about 28% (wt/wt) and about 46% (wt/wt) of the film.

5. The capsule of claim 1, wherein the glycerol comprises less than about 18% of the film by weight.

6. The capsule of claim 1, wherein the glycerol comprises less than 16% of the film by weight.

7. The capsule of claim 1, wherein the glycerol is about 14% of the film by weight.

8. The capsule of claim 4, wherein the noncrystallizing plasticizer is noncrystallizing sorbitol.

9. The capsule of claim 8, wherein the noncrystallizing sorbitol is about 36% of the film weight.

10. The capsule of claim 1, wherein the film has a dry matter content of greater than 80% by weight.

11. The capsule of claim 1, wherein the alginate comprises M alginate and G alginate, wherein the M alginate is between about 50% and about 62% by weight of M and G alginate.

12. The capsule of claim 1, wherein the fill material comprises at least one unsaturated oil.

13. The capsule of claim 12, wherein the fill material in the capsule has an oxidation rate of less than 8 TOTOX units increase per two weeks stored in open containers at 25° C./60% RH.

14. The capsule of claim 12, wherein the fill material is at least 50% (wt/wt) oil.

15. The capsule of claim 12, wherein the fill material further comprises a pharmaceutical, nutraceutical, or veterinary active agent, or a carrier therefor.

16. The capsule of claim 12, wherein the oil comprises ω-3 fatty acids, triglycerides, or salts or esters thereof.

17. A seamless alginate capsule prepared by:
   a) obtaining or preparing an emulsion comprising oil, water, optionally an emulsifier, and at least one of a water-soluble a polyvalent metal salt, and an acid, wherein the oil is present in an amount of at least 50% by weight of the emulsion;
   b) dividing the emulsion into portions;
   c) adding at least one portion of the emulsion to an aqueous gelling solution comprising alginate to form at least one wet capsule;
   d) washing the at least one wet capsule with a wash solution to form at least one washed wet capsule;
   e) contacting the at least one washed wet capsule with a plasticizing solution comprising (i) between about 2% (wt/wt) and about 18% (wt/wt) noncrystallizing sorbitol, and (ii) between about 6% (wt/wt) and about 3% (wt/wt) glycerol to form at least one plasticized wet capsule; and
   drying the at least one plasticized wet capsule, wherein: (i) the total weight of plasticizer in said film is from 35-70% by weight of the film; and (ii) said capsule has a disintegration time of less than 12 minutes in an intestinal buffer after pretreatment for 20 minutes in a solution of 0.1 M NaCl and acid (HCl) at pH of 3 at 37° C.

18. The capsule of claim 17, wherein the fill material comprises a pharmaceutical, nutraceutical, or veterinary active agent, or a carrier therefor.

19. The capsule of claim 1, wherein said capsule has a dry break strength of at least 20 kg.

20. The capsule of claim 12, wherein said pharmaceutical, nutraceutical, or veterinary agent is dispersed in said oil.

21. The capsule of claim 16, wherein said pharmaceutical, nutraceutical, or veterinary agent is dissolved in said oil.

* * * * *